United States Patent [19]

Termanini

[11] 4,154,242
[45] May 15, 1979

[54] BLADDER CATHETER

[75] Inventor: Zafer A. Termanini, Brooklyn, N.Y.

[73] Assignee: Zafmedico Corp., Brooklyn, N.Y.

[21] Appl. No.: 807,408

[22] Filed: Jun. 17, 1977

[51] Int. Cl.$^2$ ............................................. A61M 25/00
[52] U.S. Cl. ................................. 128/349 R; 128/243
[58] Field of Search ............ 128/242, 243, 348, 349 R, 128/350 R, 351, 345

[56] References Cited

U.S. PATENT DOCUMENTS

| | | | |
|---|---|---|---|
| 318,535 | 5/1885 | Bihler | 128/243 |
| 2,211,975 | 8/1940 | Hendrickson | 128/349 R |
| 2,616,429 | 11/1952 | Merenlender | 128/350 R |
| 2,688,329 | 9/1954 | Wallace | 128/349 R |
| 3,397,699 | 8/1968 | Kohl | 128/349 R |
| 3,426,744 | 2/1969 | Ball | 128/344 X |
| 3,799,172 | 9/1972 | Szpur | 128/349 R |

Primary Examiner—Dalton L. Truluck
Attorney, Agent, or Firm—Hubbell, Cohen, Stiefel & Gross

[57] ABSTRACT

Improved bladder catheter for insertion in a body cavity comprises a tubular member having a distal end and a proximal end, a longitudinally extending lumen open for drainage at the proximal end, and a plurality of circumferentially spaced longitudinally extending slits adjacent the distal end. At least the portion of the tubular member intermediate the extremities of the slits is flexible and at least one longitudinally extening spring element is disposed in each of the intermediate portions, the spring elements being unstressed when the intermediate portions are flush with the adjacent unslitted portions of the tubular member for biasing the intermediate portions to the flush position. The improved catheter also includes means within the tubular member for releasably retracting the distal end relative to the proximal end to flex the intermediate portions outwardly from the adjacent portions for retaining the catheter in the bladder. Upon release of the retracting means, the spring elements return to their unstressed state thereby returning the intermediate portions to the flush position to permit catheter withdrawal.

8 Claims, 7 Drawing Figures

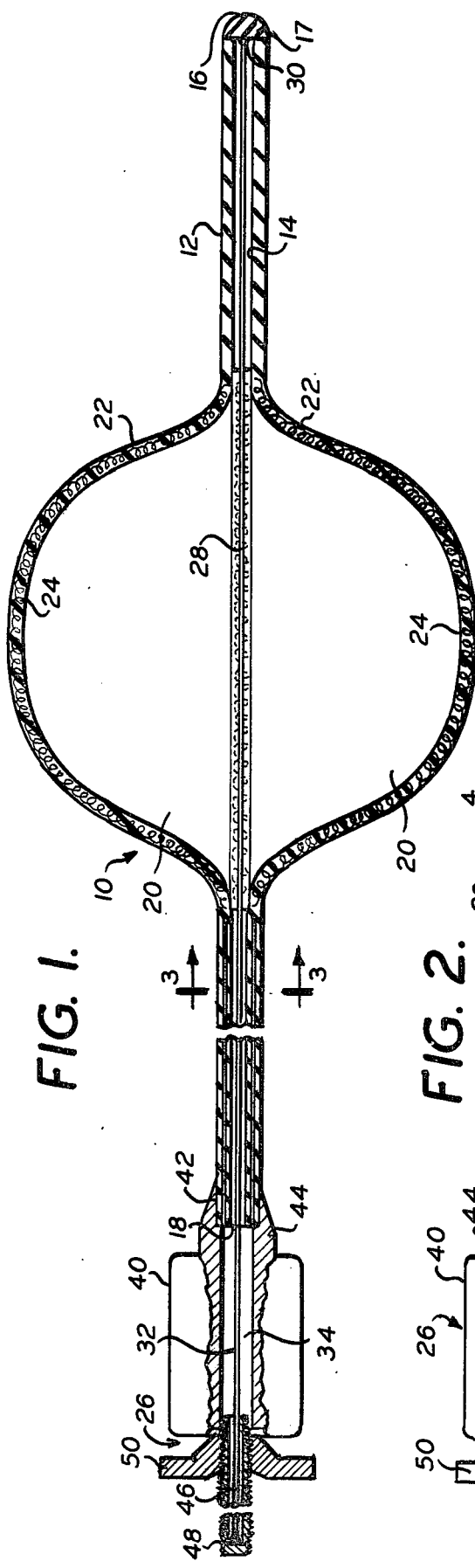
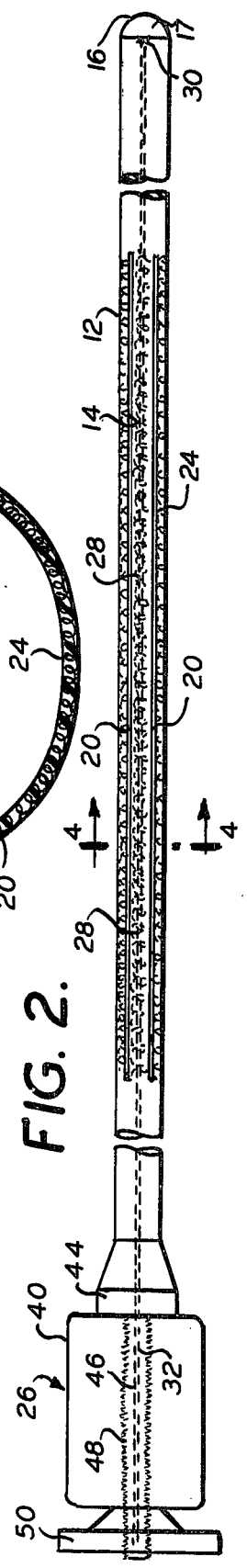
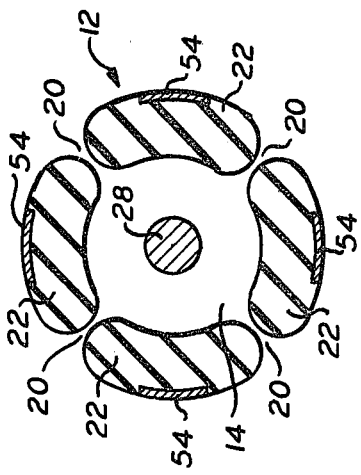
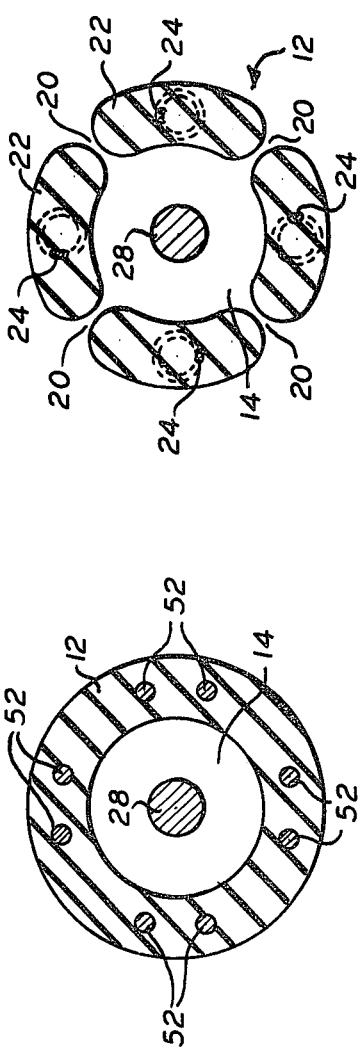

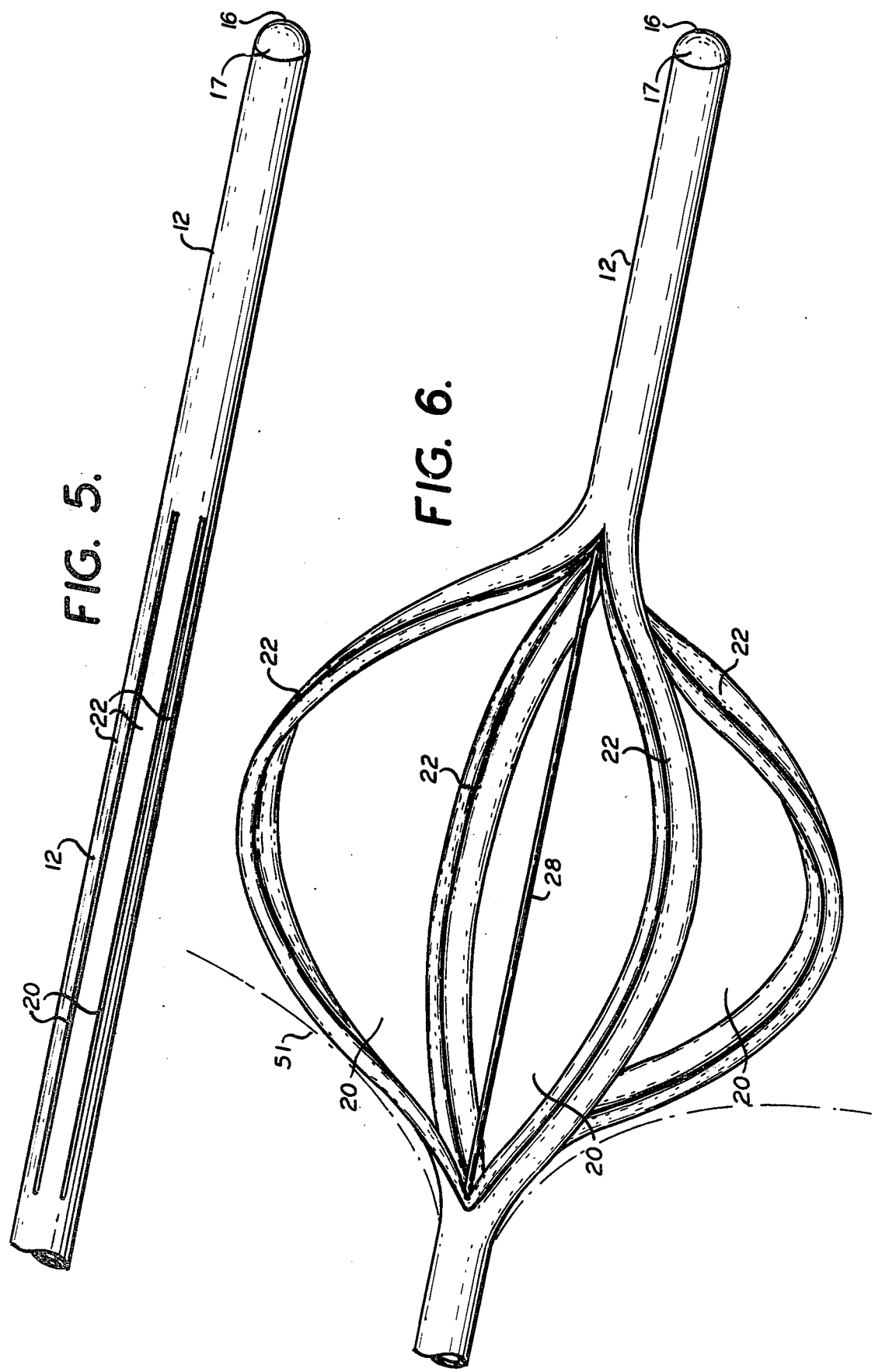

BLADDER CATHETER

BACKGROUND OF THE INVENTION

1. Field of the Invention

This invention pertains to urinary bladder catheters and more particularly to drainage type catheters incorporating retaining means.

2. Prior Art

Ideally, all drainage type urinary bladder catheters should effect complete drainage from the bladder cavity. The design of many prior art bladder catheters has, however, resulted in the accumulation of a urine pool in the bladder near its junction with the urethra. As is well known, the accumulation of such a urine pool could result in infection or even crystallization. Consequently, those prior art catheters which do not solve this problem are disadvantageous.

Bladder catheters have been designed with means for enlarging the drainage apertures or slits once the catheter has been inserted in the bladder. Upon being widened, these apertures or slits provide enhanced drainage thus avoiding the accumulation of a urine pool. Prior art catheters of this type have, however, had certain deficiencies.

Thus, U.S. Pat. No. 3,397,699 issued to Kohl discloses a flexible catheter having a plurality of longitudinal slits in a zone adjacent the distal end of the catheter. The slits define a plurality of foldable wings which are biased to radially outwardly extending positions and the portions of the catheter above and below the slits are joined together by resilient elements. In use, a stylet is inserted through the catheter lumen until the distal end thereof engages the distal end of the catheter. Sufficient force is then exerted on the distal end of the catheter through the stylet to push the portion of the catheter above the slits as far as possible from the portion below. The elastic elements are thereby stretched causing the wings to move to a position wherein they form a smooth continuation with the unslitted portions of the catheter. The catheter is then introduced into the bladder until the wings clear the interior wall thereof, whereupon the proximal end is held against movement while the stylet is gradually withdrawn. As the elastic elements retract the wings return to their outwardly extending positions and engage the bladder wall thereby retaining the catheter in the bladder. Effective drainage is accommodated through the slits which are enlarged when the wings are in their outwardly extended positions.

Kohl's catheter is disadvantageous insofar as it requires the use of a stylet or other means to stretch the elastic elements and move the wings to a flattened position to allow insertion and withdrawal of the catheter. Moreover, since the elastic elements extend longitudinally through the catheter lumen, they may interfere with the stylet during insertion and removal thereof.

U.S. Pat. No. 3,815,608 issued to Spinosa et al. discloses a bladder catheter similar to Kohl's. Thus, the wings are pretreated to assume a natural position in which they project outwardly from the body of the catheter. However, rather than employing elastic elements, Spinosa employs individual drawstrings, one for each wing, which extend through the lumen and are secured directly to the midpoints of the wings. Thus, by pulling the strings toward the proximal end, the wings are flexed to a flattened position. While this embodiment obviates the necessity of employing a stylet to effect insertion and withdrawal, the bundle of strings which extends through the lumen of the catheter may eventually interfere with effective drainage, especially with extended use. Additionally, Spinosa's catheter relies solely on the resiliency of the wings to return them to the outwardly extended positions. In the event complete return is not effected, drainage will be reduced since the spaces between the wings will be smaller, and in the extreme situation, accidental catheter withdrawal may occur.

U.S. Pat. No. 2,649,092 issued to Wallace also discloses a catheter having a plurality of longitudinally extending slits adjacent the distal end which define wings therebetween. The wings, however, are biased in a flattened position and project outwardly upon retraction of the distal end relative to the proximal end. Like Spinosa's catheter, the catheter disclosed by Wallace is disadvantageous since it relies solely on the resiliency of the material comprising the wings to return the wings to the flattened position to effect catheter removal. Complete return is highly unlikely, especially after the wings have remained in the flexed position for an extended period of time, as is often the case with catheters employed for bladder drainage. Upon failure of the wings to return completely to their unflexed position, removal of the catheter becomes extremely painful as the wings may abraid the internal walls of the urethra and the bladder.

U.S. Pat. No. 3,889,686 issued to Duturbure discloses yet another self retaining bladder catheter in which a flexible membrane extends about the tubular portion of the catheter adjacent the distal end. The tubular member includes two bores, one for the conventional drainage purpose, and the other for introducing a fluid into the flexible membrane whereby the flexible membrane may be expanded once the catheter has been inserted into the bladder. Thus, the membrane serves much the same purpose as the wings in the prior art catheters described above. One major disadvantage of this catheter is that except for a small aperture below the membrane closely adjacent the internal wall of the bladder, no other drainage ports are provided or could be provided between that point and the distal end of the membrane. Clearly, this reduces drainage and may result in the accumulation of a urine pool. Of course, the catheter may be provided with additional drainage ports located distally of the membrane. Such additional ports, however, would not enhance drainage from the portion of the bladder cavity below the distal end of the membrane. Moreover, should the aperture beneath the membrane become occluded, drainage from this portion of the bladder could be blocked altogether. Additionally, the necessity of providing two non-communicating bores in the tubular member and the introduction of a suitable fluid to expand the membrane increase both the cost and complexity of this catheter thereby reducing its commercialability.

U.S. Pat. No. 3,490,457 issued to Petersen discloses a catheter which employs a sleeve having circumferentially spaced longitudinally extending slits which sleeve is disposable about a central tubular member to provide outwardly extending wings for engaging the internal wall of the bladder and retaining the catheter therein. This catheter, however, requires the use of an obturator or stylet to effect insertion of the catheter. Moreover, Petersen's catheter, like Wallace's, relies solely on the natural resiliency of the sleeve material to return the wings to their unflexed position.

Lastly, U.S. Pat. No. 3,692,029 issued to Adair discloses a catheter wherein a compression spring disposed distally of the wings biases the wings into an outwardly extended position. A stylet is insertable through the lumen of the catheter to compress the spring and flatten the wings. Thus, this catheter is disadvantageous insofar as it requires the use of a stylet to effect insertion and withdrawal. Moreover, because the wings normally are biased in the outwardly extended position, pressure must be continuously applied to the stylet during both insertion and withdrawal to prevent internal damage to the patient.

SUMMARY OF THE INVENTION

The present invention is directed to an improved drainage-type catheter which incorporates self-retaining means, yet which may be readily withdrawn from the bladder without discomfort when desired.

The preferred catheter of the invention comprises a flexible tubular member having a longitudinally extending lumen open at least at the proximal end for drainage. The tubular member also has a plurality of circumferentially spaced longitudinally extending slits near the distal end. The portions of the tubular member between the slits and intermediate the extremities thereof define a plurality of wings.

A spring element is disposed within each of the wings and preferably extends along the entire length thereof. The springs, which are preferably of the helical variety, are unstressed when the outer surfaces of the wings are flush with the unslitted adjacent portions of the tubular member.

Means, preferably comprising a single flexible member secured at one end to the distal end of the tubular member and extending through the proximal end, are provided for releasably retracting the distal end of the catheter toward the proximal end to flex the wings to outwardly extending retaining positions. Preferably, the proximal end of the flexible member is secured to some form of retaining means for releasably securing the flexible member in the retracted position.

Thus, by retracting the flexible member once the wings have cleared the internal wall of the bladder upon insertion, the wings will engage the wall and retain the catheter therein. Further, the longitudinally extending slits, which become greatly enlarged upon flexing of the wings, permit easy and effective drainage.

When withdrawal of the catheter is desired, the flexible member is released whereupon the restoring force of the spring elements returns the wings to the flush position whereby catheter withdrawal may be effected with minimum discomfort.

It is therefore apparent that the catheter of the present invention is inexpensive to manufacture, easy to use and extremely effective for the purpose intended. These, as well as further features and advantages of my catheter will become more fully apparent from the following detailed description and annexed drawings of the preferred embodiments thereof.

BRIEF DESCRIPTION OF THE DRAWINGS

In the drawings:

FIG. 1 is a view principally in longitudinal section and partly in elevation of the preferred catheter according to the present invention with the wings in the outwardly extended or retaining position;

FIG. 2 is a view similar to FIG. 1 but with the wings in the flush position;

FIG. 3 is a sectional view taken along the line 3—3 in FIG. 1;

FIG. 4 is a sectional view taken along the line 4—4 in FIG. 2;

FIG. 5 is a fragmentary perspective view of the preferred catheter according to the present invention with the wings in the flush position;

FIG. 6 is a view similar to FIG. 5 but with the wings in the outwardly extended or retaining position; and FIG. 7 is a view similar to FIG. 4 but showing a modification of the present invention.

DETAILED DESCRIPTION OF THE PREFERRED EMBODIMENTS

Referring now to the drawings in detail and initially to FIGS. 1-6 thereof, the preferred catheter 10 according to the present invention is shown. As illustrated, catheter 10 includes a tubular member 12 having a longitudinally extending lumen 14 therein. The proximal end 18 of the tubular member 12 is open to effect drainage through the lumen 14 as will be more fully described hereinafter, while preferably, though not necessarily, the distal end 16 is closed. Preferably, tubular member 12 is comprised of a flexible resilient material such as, for example, silicone rubber.

As shown, a portion of the tubular member 12 adjacent the distal end 16 is provided with a plurality, shown by way of example as four, of longitudinally extending slits 20 which define wings 22 therebetween. As shown, a spring element 24 is embedded in each of the wings 22 and extends substantially along the length thereof. The spring elements 24 are disposed in wings 22 to asssume an unstressed position when the wings are flush with the adjacent unslitted portions of the tubular member 12 as is best illustrated in FIGS. 2 and 5. As presently preferred and shown in FIGS. 1, 2 and 4, spring elements 24 comprise helical metal springs.

As best shown in FIGS. 1 and 2, catheter 10 also includes means 26 for releasably retracting the distal end 16 of the tubular member 12 relative to the proximal end 18 to effect flexing of the wings 22 whereupon the wings assume the outwardly extended positions best illustrated in FIGS. 1 and 6. Preferably, releasable retaining means 26 includes a flexible member which preferably comprises a physiologically innocuous monofilament such as a nylon or polypropylene fiber cord or string 28. As shown, member 28 extends through lumen 14 and is secured at one end 30 to a cap 17 which is fixedly secured to the distal face of tubular member 12 thereby sealing the distal opening thereof. Cap 17 may be secured to tubular member 12 by, for example, an adhesive. Member 28 may be secured to cap 17 in a similar manner. Preferably, the distal face of cap 17 is rounded to facilitate insertion of the catheter.

As shown and preferred, the proximal end 18 of the tubular member 12 is received and secured in a cylindrical recess 42 of a member 44 which protrudes from one side of a housing 40. The other end 32 of the flexible member 28 extends beyond the proximal end 18 of tubular member 12, through a bore 34 in the housing 40 and is received and secured in an axial recess 46 in a threaded bolt 48 which bolt is partially slidably received in the bore 34 and is secured to housing 40 by the wing nut 50.

It is thus apparent that rotation of wing nut 50 in one direction will effect movement of the bolt 48 out of the bore 34. The resulting retraction of the string 28 results in relative movement of distal end 16 toward proximal end 18 whereupon the wings 22 assume their outwardly extended positions.

It is similarly apparent that rotation of the nut 50 in the other direction effects movement of the bolt 48 into the bore 34. The slack thereby created in the cord 28 permits relative movement of the distal end 16 of tubular member 12 away from the proximal end 18 which movement is effected by the resiliency of both the spring elements 24 and the wings 22. Clearly, upon sufficient rotation of the nut 50, the bolt 48 will be substantially completely received within the bore 34 and the wings 22 will assume their flush positions as is best illustrated in FIGS. 2 and 5. Of course, in the event tubular member 12 is comprised of a flaccid material, movement of the wings 22 to their flush positions will be effected solely by the resiliency of the springs 24.

In use, catheter 10 is initially in the position illustrated in FIGS. 2 and 5. The distal end 16 of the catheter 10 is then fed through the urethra into the bladder until at least the proximal side of the wings 22 is completely received within the bladder cavity. Since tubular member 12 is comprised of a flexible material, little or no discomfort will be associated with insertion.

After insertion is complete, the nut 50 is rotated to the position illustrated in FIG. 1 to retract the distal end 16 of the tubular member 12 toward the proximal end 18. This results in movement of the wings 22 to the outwardly extended position illustrated in FIGS. 1 and 6 which movement is accommodated by longitudinal slits 20. As best shown in FIG. 6, in this position the proximal portions of the wings 22 engage the internal wall 51 of the bladder thereby retaining the catheter 10 therein. Clearly, as the wings 22 expand, the slits 20 become enlarged whereby when the catheter 10 assumes the position illustrated in FIG. 6, easy and effective drainage is accommodated through slits 20 and lumen 14. Assuming the catheter is located with the proximal ends of the wings 22 substantially flush with the inside wall of the bladder, complete drainage will be achieved without any trapped pool remaining as a potential site of infection or crystallization. Of course, suitable means (not shown) in communication with the distal end 18 of the lumen 14 will be provided for effecting drainage therefrom. If desired, additional drainage apertures may be provided in the tubular member 12 between the distal end 16 thereof and the distal extremities of slits 20.

When withdrawal of catheter 10 is desired, nut 50 is simply rotated to effect movement of bolt 48 into bore 34 whereupon the distal end 16 of the tubular member 12 moves away from the proximal end 18 as is more fully described above. Thanks to springs 24, complete return of the wings 22 to the flush position illustrated in FIGS. 2 and 6 is assured, thus permitting easy and relatively painless withdrawal of catheter 10 from the bladder and urethra.

As illustrated in FIG. 3, preferably, although not necessarily, the sheath of tubular member 12 proximal of the wings 22 includes a plurality of elongate semi-rigid members 52 embedded therein. The members 52 provide additional support for the proximal portion of the tubular member 12 thereby preventing undue and unnecessary flexing thereof.

Skilled art workers will appreciate that while spring elements 24 have been described as helical springs, other springs, while not preferred, may be employed. For example, with particular reference to FIG. 7, helical springs 24 have been replaced by leaf springs 54 disposed in the outer portions of the wings 22. It is apparent that the leaf springs 54 seve the same function as helical springs 24, that is, to insure return of the wings 22 to the fully flush position illustrated in FIGS. 2 and 5 to permit easy withdrawal of catheter 10. However, leaf springs are not preferred since breakage of the leaves followed by delamination thereof could cause severe damage to the bladder and urethra. Wire springs comprise a still further alternative but possess the same disadvantages as leaf springs.

In addition, while spring elements 24 are preferably comprised of metal, plastic spring elements, while less advantageous, may also be used. Specifically, plastic springs are not preferred since they may take on a set with extended periods of deflection. Similarly, while tubular member 12 is preferably comprised of silicone rubber, latex, or for that matter any suitable elastomeric material, may be effectively employed. Also, while tubular member 12 is preferably comprised of the same material throughout, this is not necessary and wings 22, for example, may be comprised of a more flexible material than the remainder of the tubular member 12 to further facilitate movement of the wings 22 between the flush and outwardly extended positions.

Since these as well as other modifications and changes are within the scope of the present invention, the above description should be construed as illustrative and not in the limiting sense.

I claim:

1. In a catheter for insertion in a body cavity of the type comprising a tubular member having a distal end and a proximal end, a longitudinally extending lumen open at said proximal end, and means for releasably retaining said tubular member in said body cavity, said retaining means being defined by a plurality of circumferentially spaced longitudinally extending slits in said tubular member adjacent said distal end, at least the portions of said tubular member intermediate the extremities of said slits being flexible, the improvement comprising:

spring means embedded in each of said intermediate portions, said spring means being unstressed when said intermediate portions are flush with the adjacent unslitted portions of said tubular member for biasing said intermediate portions to said flush position; and means for releasably retracting said distal end relative to said proximal to flex said intermediate portions and said spring means outwardly from said adjacent portions, said spring means returning to their unstressed position upon release of said retracted means whereby said intermediate portions are returned to said flush position.

2. The catheter of claim 1, wherein said spring means comprise helical metallic springs.

3. The catheter of claim 2, wherein said helical springs extend substantially throughout the lengths of their respective intermediate portions.

4. The catheter of claim 3, wherein said entire tubular member is comprised of an elastomeric material.

5. The catheter of claim 4, wherein said releasable retracting means comprises a flexible member disposed in said lumen and secured at one end to the distal end of said tubular member; and means secured to the other end of said flexible member for retracting said flexible member through said lumen and releasably retaining said flexible member in said retracted position.

6. The catheter of claim 5, wherein said flexible member is a monofilament comprised of a physiologically innocuous material.

7. The catheter of claim 6, wherein said monofilament retracting means comprises a rigid member fixed relative to said tubular member and having an aperture therein, bolt means extending through said aperture, said other end of said monofilament being secured to said bolt means, and nut means for engaging said bolt means and said rigid member for securing said bolt means relative to said rigid member, whereby rotation of said nut mean in one direction effects movement of said bolt means through said aperture away from said proximal end to thereby retract said monofilament, and rotation of said nut means in the other direction effects movement of said bolt means through said aperture toward said proximal end to release said monofilament from said retracted position.

8. The catheter of claim 1, and further comprising a plurality of longitudinally extending support members less flexible than said tubular member, said support members being disposed in said tubular member adjacent the proximal extremities of said slits.

* * * * *